United States Patent [19]

Traynor

[11] Patent Number: 4,602,090

[45] Date of Patent: Jul. 22, 1986

[54] POLYMETHYLENE PYRROLES

[75] Inventor: Lee Traynor, Akron, Ohio

[73] Assignee: The B. F. Goodrich Company, Akron, Ohio

[21] Appl. No.: 679,846

[22] Filed: Dec. 10, 1984

Related U.S. Application Data

[62] Division of Ser. No. 494,752, May 16, 1983, Pat. No. 4,487,667.

[51] Int. Cl.$^4$ .................. C07D 401/06; C07D 209/52

[52] U.S. Cl. .................................. 546/272; 548/452; 548/466

[58] Field of Search ...................... 548/452, 466, 468; 546/272

[56] References Cited

PUBLICATIONS

Index Guide to Chemical Abstracts introduction vol. 76, pp. 451, 301, 302.

*Primary Examiner*—Jane T. Fan

*Attorney, Agent, or Firm*—Alfred D. Lobo; James R. Lindsay

[57] ABSTRACT

Cycloalk-2-enes and cycloalk-2-ene-dienes are found to be Michael acceptors which react with tosylmethylisocyanide to form bicyclo fused-ring compounds. A wide variety of substituents may be introduced on the alkylene ring with the aid of the carbonyl group(s) on the fused-ring compound.

These carbonyl-containing bicyclo fused-ring compounds may be reduced to provide monomers which may be electrodeposited as substituted polypyrroles ("PP") which are electrically conductive, compactable and extrudable organic polymers. By choice of substituents on the alkylene ring which bridges the 3- and 4-carbon atoms of the pyrrole ring, the PP may be tailored for use either as a semiconductor having a conductivity in the range from about $10^{-5}$ to about $10^{-2}$ S/cm, or a relatively good conductor having a conductivity in the range from about $10^{-2}$ to about $10^{2}$ S/cm.

A method is disclosed for preparing a polymethylene-substituted pyrrole comprising reacting a cyclic mono- or di-ketone Michael acceptor selected from the group consisting of cycloalk-2-enes and cycloalk-2-dienes, with tosylmethylisocyanide, in the presence of a solvent, so as to form an azabicycloalkylene(di)one, directly, without substituting the N-adjacent carbon atoms on the pyrrole ring.

3 Claims, No Drawings

POLYMETHYLENE PYRROLES

This is a division, of application Ser. No. 494,752, filed May 16, 1983, now U.S. Pat. No. 4,487,667 issued Dec. 11, 1984.

BACKGROUND OF THE INVENTION

This invention relates to organic conductors and semiconductors which fall into the group of polymeric conductors. As is well known, such conducting polymers appear in some respects like common synthetic resinous materials, but unlike such common materials (plastics), conducting polymers defy conventional melt-processing, cannot be compacted, whether molded or extruded, in the usual ways, nor deposited as a continuous film from solution, and are far from stable in air even at ambient temperature conditions. As long as a polymer is formed by electrodeposition on an electrode its conductivity may be said to be fair depending upon the particular application for which the polymer is sought. But a polymer which defies compaction into a shaped article, places severe limitations upon its use. Because a compactable conductor (the term "conductor" as used herein includes semiconductors) is far more versatile in its applications, the problem was to find a compactable polymer.

Tinkering with the structure of conducting polymers to improve their processability, for example by introducing substituents, generally results in degradation of their already low conductivity, consistent with the belief that conductivity is along the polymer chains. Low conductivity in the range from about $10^{-5}$ to about $10^{-2}$ $ohm^{-1}cm^{-1}$(reciprocal ohms/cm is hereafter designated "S/cm" for convenience) places a conductor in the category of semiconductors, while conductivity in the range from about $10^{-2}$ to about $10^{2}$ S/cm and above places it in the category of relatively good conductors. Of course, such "low conductivity" is referred to as such only in relation to the high conductivity of metals, but this low conductivity is sufficiently high for a variety of applications, for example, as polymer films on electrodes, as is described in articles titled "Polymer Films on Electrodes. 6. Bioconductive Polymers Produced by Incorporation of Tetrathiafulvalenium in a Polyelectrolyte (Nafion) Matrix" by Henning, T. P., White, H. S., and Bard, A. J., *J. Am. Chem. Soc.,* 103 3937–38, (1981); and, "Polymer-Modified Electrodes: A New Class of Electrochemical Materials", by Kaufman, F. B., Schroeder, A. H., Engler, E. M., and Patel, V. V. *Appl. Phys. Lett.,* 36(6), 422–5, (1980).

Poly(2,5-pyrrole), also referred to herein as "PP" for brevity, in which the —NH— group links sequences of conjugated double bonds, is normally an insulator, that is, has a conductivity less than about $10^{-10}ohm^{-1}cm^{-1}$ and is totally insoluble in known solvents. It is known however, that electrochemically polymerized PP has good conductivity, but coupled with its melt-processing-resistance and the poor integrity of PP film so formed, the metamorphosis of PP into a practical organic polymer conductor poses a formidable problem. Moreover, it is generally known that providing substituents on the pyrrole monomer does not improve the conductivity of PP. This is not undesirable with respect to tailoring a semiconductor but contraindicates a logical course of action for tailoring a relatively good conductor.

The interest in modification of electrode surfaces by covalently attaching an organic monolayer or by depositing a polymer film spurred the electrochemical polymerization of pyrrole under controlled conditions as reported in "Electrochemical Polymerization of Pyrrole" by Diaz, A. F. et al in *J. C. S. Chem. Comm.* 1979, 14, 635. The films may be prepared in a variety of aprotic solvents but are totally insoluble in known solvents including acetonitrile (MeCN), methylene chloride and propylene carbonate. Subsequently, PP with p-type conductivity of 100 S/cm was prepared which were stable in air. These films were prepared from MeCN solution using a tetraethylammonium tetrafluoroborate electrolyte, as described in "Organic Metals: Polypyrrole a Stable Synthetic 'Metallic' Polymer" by Kanazawa, K. K. et al in *J. C. S. Chem.* 1979, 15, 854. Because the polymer film remains on the electrode surface as it is generated, the ability of the PP film to conduct is critical for the continuation of the reaction forming the film. Considerations related to the forming of the film, the electroactive behavior of thin films, and other details are discussed in "Electrochemical Preparation and Characterization of Conducting Polymers" in *Chemica Scripta.,* 1981, 17 145–148.

Particularly noteworthy is that PP requires no dopant because it is naturally positively charged indicating it already has an electron removed during polymerization. Even more noteworthy is that PP films which were formed with various substituents on the N-atom were also totally insoluble. The magnitude of this limitation may only be gauged in terms of the limited application of any polymer which requires that it be electrodeposited on an electrode as a film, and which must be used in no other but the film form. At best, film of known PPs is difficulty powdered, and such powders as are formed cannot be pressed into a coherent shaped article even at 100,000 psi.

Despite knowing that substituents on the pyrrole ring would diminish conductivity, and recognizing that the 2- and 5- positions must necessarily remain open if the substituted pyrrole is to be polymerized, I surmised that the possibility of making compactable PP might hinge upon my finding the correct combination of substituents on the pyrrole nucleus. I further hoped that such a 3- and/or 4- substituted pyrrole would lend itself to electrochemical polymerization with an appropriate electrolyte which might favorably affect the solubility of the polymer formed. As will presently be evident, I was successful in the preparation of compactable polypyrroles, but they were essentially insoluble in known solvents.

Of particular interest was that, knowing a substituted pyrrole can be made in which the substituents in the 3- and 4- positions were cyclized ("3,4-cyclized pyrrole"), the fact is that the strain on the molecule is great. Such a strained molecule is unlikely to withstand a reduction reaction without affecting its strained condition. This is substantiated by the fact that such bicyclo fused-ring pyrroles are not known except for those disclosed in articles titled "Synthesis of Isobenzofuran-4,7-quinone and Isoindole-4,7-quinone" by Cragg et al, *J. Chem. Soc. Perkin Trans.* 1975, (14) 1339–42; and, "Stable Quinoid Derivatives of Isobenzofuran and Isoindole" by Giles et al, *J. Chem. Soc. Chem. Commun.* 1975, (7) 260.

Making such compounds by the method described in the foregoing references is impractical. Further, it will be noted that in a compound having the foregoing structure, there are oppositely disposed carbonyl groups in the ring which has a single double bond, and even if a method is found to reduce the compound, this double bond would still endure.

Since this product of interest is the PP polymer, it is necessary that the N-adjacent carbon atoms (that is, the C atoms in the 2- and 5- positions) be left open. There was nothing to suggest that if a polymethylene group could bridge (that is, be cyclized with) the 3- and 4- C atoms of the pyrrole ring, the resulting bicyclo compound would, when polymerized, because of the polymethylene bridge, be transformed from incompactable PP to compactable PP, if indeed the substituted PP proved to be electrically conductive. Nor was there anything to suggest that the critical polymethylene bridge might, with the proper choice of additional substituents on the bridge, lend the PP both solubility and enhanced conductivity.

I polymerized several compounds I made for the specific purpose of studying the electronic effects of substituents on conductivity, and it was only by chance that I discovered the criticality of the polymethylene bridge. This led me to seek and find an appropriate method of preparing a cyclic 3,4-polymethylenepyrrole, particularly tri- and tetramethylene pyrroles (hence "T-P" for brevity), some of which were particularly suitable for electropolymerization, and some of which are useful microbicides.

Accordingly, I cast about for a method of forming the polymethylene bridge between the 3- and 4- C atoms of the pyrrole ring and unexpectedly discovered that a cycloalk-2-enone would react with tosylmethylisocyanide so as to form a pyrrole ring resulting in a bicyclo fused ring carbonyl compound. Such a ring closure was known to occur with acyclic esters, ketones and nitriles in the van Leusen procedure (see "A New and Simple Synthesis of the Pyrrole Ring System from Michael Acceptors and Tosylmethylisocyanides" by van Leusen, A. M. et al, *Tetrahedron Letters,* No. 52, pp. 5337-5340, 1972). That there is a peculiarity about the reaction with a cycloalk-2-enone stems from the discovery that the presence of the alkylene ring does not prevent the cyclization of the vinyleen C atoms to yield a bicyclo fused-ring compound.

Further, though I was aware that a "Michael condensation" between a cycloalk-2-enone and certain compounds was feasible with an appropriate catalyst, there was no indication that the cycloalk-2-enone might behave as it does, because one would expect that the monocyclic Michael condensation product would be unlikely to form a strained bicyclo fused-ring product. The peculiarity of this reaction as it does actually occur, permits the cyclization of the condensation product's vinylene C atoms into a pyrrole ring. See "*The Michael Reaction*", *Organic Reactions* Vol. 10, 187 et seq., John Wiley & Sons (1959).

Having succeeded in making the desired 3,4-cyclized pyrrole from a cycloalk-2-enone which was a Michael acceptor, I reduced the carbonyl reaction product and electropolymerized it. Finally, I tested the PPs for electrical properties, and most of all, for compactability, and/or solubility in available solvents.

SUMMARY OF THE INVENTION

I have discovered that bicyclo fused-ring 3,4-polymethylene substituted pyrroles may be produced quite easily, optionally with a wide variety of substituents, and that these compounds include monomers which may be polymerized, by linking through N-adjacent C atoms, to form electrically conductive polypyrrole ("PP") polymers which are compactable and deformable upon compaction.

Moreover, such PPs are quite easily prepared by conventional electrochemical deposition with appropriate substituents. By choice of the substituent(s) on the polymethylene ring the PP may be tailored for use either as a semiconductor having a conductivity in the range from about $10^{-5}$ to about $10^{-2}$ S/cm, or a relatively good conductor having a conductivity in the range from about $10^{-2}$ to about $10^{2}$ S/cm.

It is therefore an object of this invention to provide novel electrically conductive PP homopolymers which are generally electrodeposited as powders which are compactable, that is, pressable or extrudable into shaped articles. The PPs are derived from a monomer having a structure selected from the group consisting of

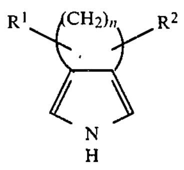

(I)

and

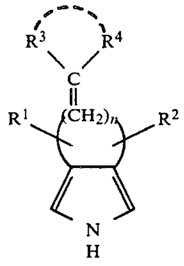

(II)

wherein, n is an integer chosen from 3 and 4, so that at least one C atom carrying a substituent in the polymethylene ring is not adjacent to the 3- and 4- C atoms on the pyrrole ring;

$R^1$ and $R^2$, if present, are independently selected from phenyl, hydroxyphenyl, cycloalkyl having from 4 to about 7 carbon atoms, lower alkyl, alkoxy and hydroxyalkyl each having from 1 to about 6 carbon atoms, and each substituent may be on the same C atom, or different C atoms, distally located from the 3- and 4- C atoms of the pyrrole ring; and, $R^3$ and $R^4$ independently represent H and acyclic moieties which may be cyclized, and aromatic or heteroaromatic moieties which may be substituted, and, if $R^3$ and $R^4$ are each cyclic, they may be connected with a cyclized substituent.

It has further been discovered that cycloalk-2-enones and cycloalk-2-ene-diones (for convenience, together referred to herein as "cycloalk-2-en(di)ones") which, although normal Michael acceptors, are unexpectedly also susceptible to a ring-closure reaction with tosylmethylisocyanide in which the vinylene C atoms become part of a pyrrole ring.

It is therefore also a general object of this invention to provide a synthesis of bicyclo fused ring 3,4-polymethylene pyrroles in which further substituents may be introduced, comprising, reacting substantially equimolar amounts of tosylmethylisocyanide with a cycloalk-2-en(di)one in the presence of a mutual solvent, and with an effective amount of a strong base selected from the group consisting of an alkali metal hydride, ethoxide, or amide, at ambient temperature and pressure, so as directly to form bicyclo fused ring compounds with carbonyl-containing alkylene rings which, upon reduction yield compounds with the structures (I) or (II) in which the 2- and 5-positions are kept unsubstituted.

DETAILED DESCRIPTION OF PREFERRED EMBODIMENTS

In one embodiment of the invention, a bicyclo fused-ring pyrrole is prepared by reacting a cycloalk-2-enone or a cycloalk-2-ene-dione selected from the group consisting of compounds represented by the structures

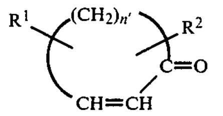

(III)

and

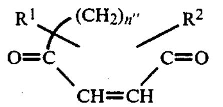

(IV)

wherein,

- n is an integer chosen from 2 and 3;
- n" is an integer chosen from 1 and 2; and,
- $R^1$ and $R^2$, if present, are independently selected from phenyl, hydroxyphenyl, cycloalkyl having from 4 to about 7 carbon atoms, lower alkyl, alkoxy and hydroxyalkyl each having from 1 to about 6 carbon atoms, and each substituent may be on the same C atom, or different C atoms, and both $R^1$ and $R^2$ cannot be on C atoms adjacent to the 3- and 4- C atoms of the pyrrole ring; with, tosylmethylisocyanide ("TosMIC") in the presence of a solvent, at a temperature and pressure sufficient to form a bicyclo, fused-ring pyrrole in which the alkylene ring has at least one carbonyl adjacent the 3- or 4- C atoms of the pyrrole ring, and the alkylene ring may optionally have additional substituents. The bicyclo fused rings are formed directly without substituting the pyrrole ring in the 2- and 5- positions.

The solvent for TosMIC is typically a mixture of equal parts by volume of diethylether and dimethylsulfoxide, and the reaction is conveniently carried out at room temperature and pressure. In some cases it is desirable to increase the temperature to accelerate the reaction and a temperature as high as about 100° C. or higher may be used in a pressure vessel which contains the autogenous pressure build-up.

Illustrative of the foregoing synthesis are the conversions of the following cycloalk-2-en(di)ones to the corresponding bicyclo fused ring pyrroles:

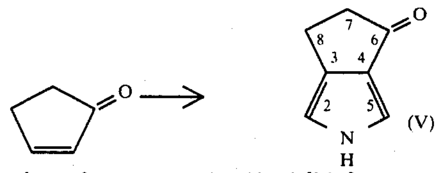

(V)

cyclopent-2-enone → 1-azabicyclo[3,3,0]octa-2,4-diene-6-one

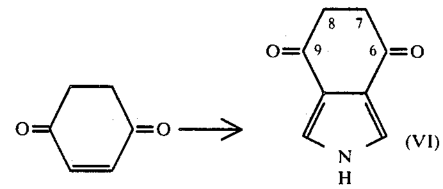

(VI)

cyclohex-2-enone-1,4-dione (2,3-dihydrobenzoquinone) → 1-azabicyclo[3,4,0]nona-2,4-diene-6,9-dione

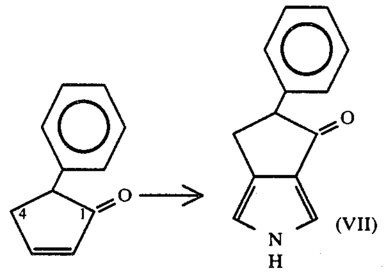

(VII)

5-phenyl-cyclopent-2-enone → 7-phenyl-1-azabicyclo[3,3,0]octa-2,4-diene-6-one

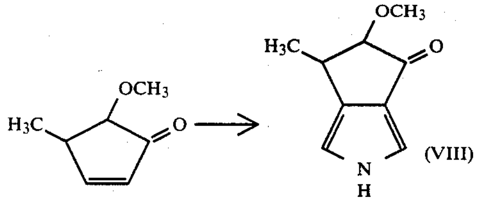

(VIII)

4-methyl-5-methoxy-cyclopent-2-enone → 7-methoxy-8-methyl-1-azabicyclo[3,3,0]octa-2,4-diene-6-one

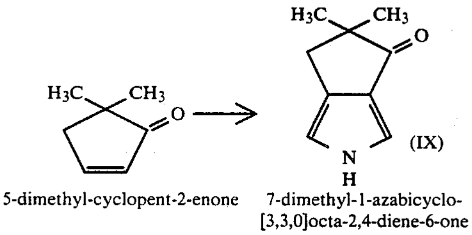

(IX)

5-dimethyl-cyclopent-2-enone → 7-dimethyl-1-azabicyclo-[3,3,0]octa-2,4-diene-6-one With the synthesis of this invention it will now be evident that known bicyclo mono- and di-ketones, optionally with desirable substituents, are convenient starting materials for reaction with TosMIC in the presence of solvent and NaH, to form a large variety of substituted polymethylene, particularly trimethylene- and tetramethylene-pyrroles in which one or both of the 'proximal' C atoms of the alkylene ring (namely, one or both those adjacent the 3- and 4- C atoms of the pyrrole ring) are carbonyl. These substituted bicyclo fused-ring ketones are referred to herein as "TP-(di)ones" for brevity. A dione starting material is used where substituents on plural distally located C atoms are desired, and the introduction of such substituents depends upon the electronic influence of the carbonyl groups.

The foregoing TP-(di)ones may be represented generally by the structures

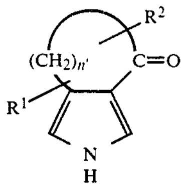

(X)

and

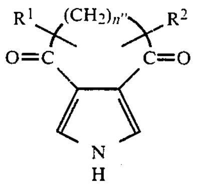

(XI)

wherein, n', $R^1$ and $R^2$ have the same connotation as hereinbefore.

As illustrated hereinabove, substituents on the alkylene ring may be provided on the cyclo-alk-2-en(di)one starting material prior to reacting with TosMIC to form the TP-(di)one. Lower alkyl, alkoxy and hydroxyalkyl substituents may be conveniently introduced on the cycloalk-2-en(di)one, but cyclic substituents such as benzyl, phenyl, cyclohexyl, pyridyl and thiophenyl are more conveniently introduced after formation of the TP-(di)one by virtue of the electronic effect of the carbonyl group(s). Thus, when in addition to the substituents $R^1$ and $R^2$, another substituent X is introduced on the alkylene ring after formation of the TP-(di)one, whether such X substituent is connected to the ring with a single bond or a double bond, the TP-(di)ones may be represented by the structures:

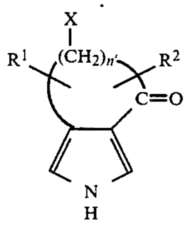

(XII)

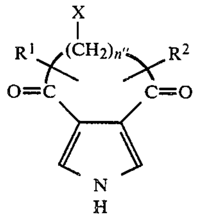

(XIII)

wherein, X represents

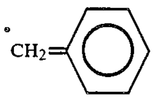 and 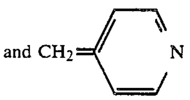

which are connected to the ring with a single bond; and, $=CH-(C_nH_{2n+1})$ 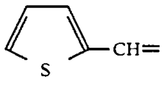 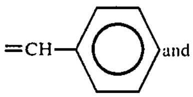 and

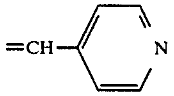

which are connected to the ring with a double bond; and, n, n'', $R^1$ and $R^2$ have the same connotation as that given hereinabove.

The substituent X may optionally be substituted, for example, with halogen, preferably chlorine and bromine, and lower alkyl, hydroxyalkyl, or alkoxy each having from 1 to about 6 carbon atoms. Halogen substituents enhance antimicrobial activity. Alkyl and alkoxy substituents contribute to polymers having higher molecular weights, but unfortunately do not lend the polymers significant solubility in any commercially available solvents.

Illustrative of the TP-(di)ones having the foregoing substituents are the following:

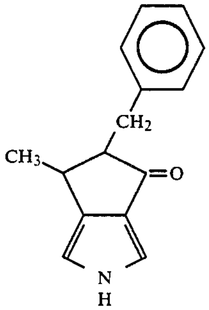

(XIV)

7-benzyl-8-methyl-1-azabicyclo[3,3,0]octa-2,4-diene-6-one

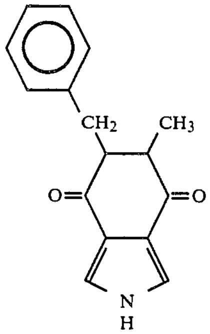

(XV)

7-methyl-8-benzyl-1-azabicyclo[3,4,0]nona-2,4-diene-6,9-dione

-continued (XVI)

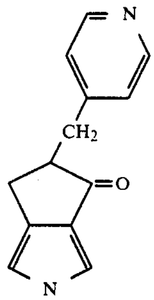

7-(4-pyridylmethyl)-1-azabicyclo[3,3,0]octa-2,4-diene-6-one (XVII)

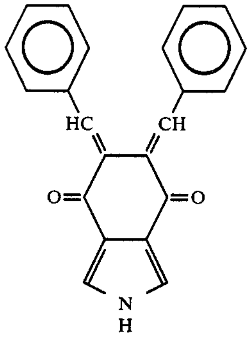

bis[7,8-benzylidene]-1-azabicyclo[3,4,0]nona-2,4-diene-6,9-dione (XVIII)

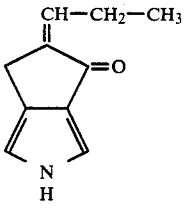

7-propylidene-1-azabicyclo[3,3,0]octa-2,4-diene-6-one (XIX)

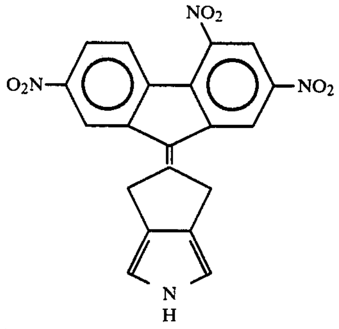

7-(trinitro-9-fluorenylidene)-1-azabicyclo[3,3,0]octa-2,4-diene-6-one (XX)

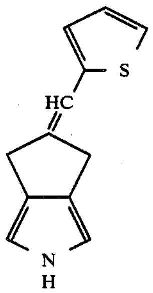

7-(2-thiophenemethylene)-1-azabicyclo[3,3,0]octa-2,4-diene-6-one

These TP-(di)ones are antimicrobial agents, the effectiveness of which will vary depending upon the particular substituents on the alkylene ring. It will readily be recognized that, because of steric considerations, making compounds with some combinations of substituents will be easier than others.

The TP-(di)ones having the foregoing structures (X), (XI), (XII) and (XIII) may be reduced, for example, by heating to about 160°-200° C. with hydrazine and KOH in diglyme solvent, or with a metal hydride such as $LiAlH_4$ in tetrahydrofuran (THF). Thus, reduction of the foregoing compounds by any suitable known reaction, results in compounds having the following structure (XXI)

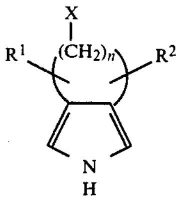

and the foregoing structure (I)

wherein, n, $R^1$ and $R^2$ have the connotation given hereinbefore; and,

X, if present, also has the same connotation given hereinabove.

With some substituents it is found that the direct reduction with metal hydride is not as effective as first protecting the N atom, for example, by tosylating the TP-(di)one, followed by heating with lithium diisopropylamide, then adding the appropriate reactant to introduce the X substituent desired, and finally reducing with hydrazine and KOH in diglyme solvent at about 180° C. The sequence is illustrated as follows:

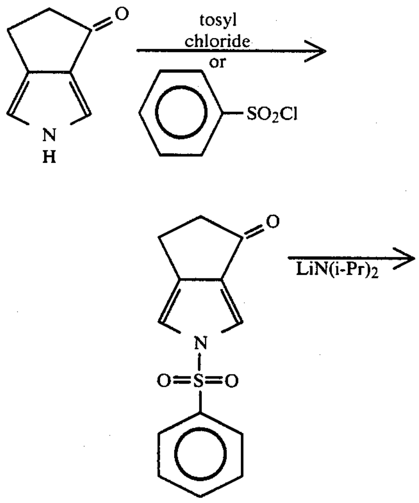

-continued

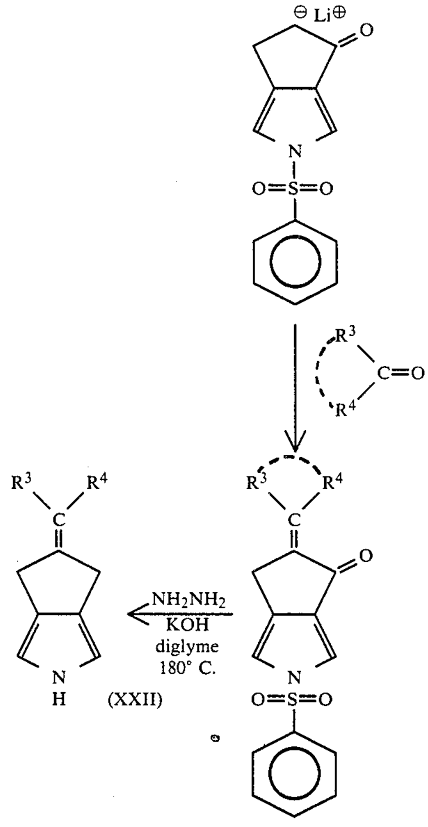

(XXII)

The foregoing reduced compounds are also antimicrobial agents, their effectiveness again depending upon the substituents on the alkylene ring, which substituents, quite fortuitously, are generally not affected by the reduction reaction.

The reduced compounds may also be used as monomers for the preparation of electrically conductive polymers, by electrodeposition. The conductive polymers of this invention may be represented by a structure selected from

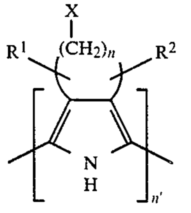
(XXIII)

and

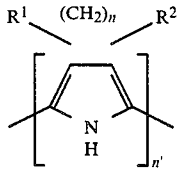
(XXIV)

wherein, n' is an integer in the range from 2 to about 100, and more preferably in the range from about 20 to about 80;

n is an integer in the range from 3 to about 5, so that at least one C atom in the polymethylene ring is distally located relative to the 3- and 4-C atoms on the pyrrole ring;

$R^1$ and $R^2$, if present, are independently selected from phenyl, hydroxyphenyl, cycloalkyl having from 4 to about 7 carbon atoms, lower alkyl, alkoxy and hydroxyalkyl each having from 1 to about 6 carbon atoms, and each substituent may be on the same C atom, or different C atoms, distally located from the 3-and 4- C atoms of the pyrrole ring; and, X, if present, has the same connotation as that given hereinabove.

In carrying out the electrochemical deposition of the polymer, one preferred method comprises electrochemically oxidizing the ether-substituted pyrrole in a manner analogous to that known for producing PP "pyrrole black" from pyrrole (see "Electrochemical Polymerization of Pyrrole", by Diaz, A. F. et al, *J.C.S. Chem. Comm.*, 1979, 635-636). The PP is formed as a powdery deposit which remains on the electrode surface and no significant slow-down of polymer build-up is noted as the electrodeposition continues. Because it so happens that the PP powder is compactable, it is fortuitous that the PP is generally deposited as a powder. In some cases, depending upon the choice of substituents and conditions of electrodeposition, a PP film may be formed. As will be appreciated, when a film is formed, as is the case with known PPs, build-up of the film on the electrode will tend to insulate the electrode, slowing deposition of the polymer.

It will not as easily be appreciated that conventional PP film cannot be transformed into another shape. It yields an unsatisfactory powder which does not lend itself to being either compacted into discs or plates, or extruded into strips or rods of arbitrary length. It is therefore regarded as being non-compactable and non-deformable.

As will be readily evident, the total insolubility of known PPs dictates that it cannot be cast from a solvent; nor can its molecular weight be measured by conventional techniques.

The known stoichiometry of the oxidation reaction during electrodeposition, combined with the insolubility of the powdery deposit in the electrolyte permits continuous deposition of the powder. Where a film is formed, which occurs with certain substituents more easily than others, and which is also a matter of the choice of electrolyte and electrodeposition conditions chosen, the desired thickness of the film may be controlled by monitoring current density of the reaction. In general, the polymer is formed as a powder which is scraped off the electrode at intervals, and compacted or extruded under sufficient pressure and at elevated temperature, to produce the shaped article desired.

It is preferred that the PP be produced under an inert blanket such as a $N_2$ atmosphere, in a three electrode, undivided electrochemical cell using palladium, platinum or other noble metal electrodes for the working and counter electrodes, and a standard calomel reference electrode (SCE), for the purpose of monitoring the current. Of course, on a production scale, stainless steel electrodes may be desirable and other methods of monitoring the current may be used, so that the reference electrode may be dispensed with.

Acetonitrile (MeCN) and propylene carbonate are preferred solvents for the monomer, though any other solvent with an acceptable dielectric constant may be used, as long as the solvent is also a solvent for the electrolyte. Preferred solvents are those with relatively high dielectric constants in the range above about 30, such as dimethylformamide (DMF), dimethylsulfoxide (DMSO), methanol, nitromethane and the like. Preferred electrolytes are those which, in solution, contribute a strong acid ion, such as tetraalkylammonium salts of tetrafluoroboric, hexafluorophosphoric and sulfuric acids, the most preferred being alkylammonium hydrogen sulfates such as tetrabutylammonium hydrogen sulfate, and alkylammonium sulfonates such as tributylammonium m-nitrobenzene sulfonate.

It has been found that propylene carbonate is the most preferred medium for electropolymerization of the monomer. The thickness of the powdery deposit is arbitrary but where films are formed, they are typically in the range from about 0.01-0.2 mm thick. Both the film and powder adhere to the electrode displaying good conductivity in the range from about $10^{-2}$ to about 10 S/cm. The polymer was deposited for experimental purposes at constant potential on a 75 $cm^2$ platinum electrode.

Elemental analyses indicate the novel PPs are composed of about 60–95% by weight of pyrrole units, the remaining being the anion (preferably $HSO_4^-$) from the electrolyte used, and trace amounts of contaminants. The PP accounts for from about 90–99% by wt of the polymer formed.

The electropolymerized PP is found to be oxidized to the extent of one positive charge for every two to about four (2–4) pyrrole units. The PP is stable at room temperature and up to about 150° C. which is also a characteristic of other known PP films.

EXAMPLE 1

One equivalent (82 g) of cyclopent-2-enone is reacted with an equivalent of TosMIC in $Et_2O$/DMSO in the presence of sodium hydride or other strong base to form a TP-one, namely, 1-azabicyclo[3,3,0]octa-2,4-diene-6-one, the reaction occurring at room temperature. Water is added and the aqueous phase continuously extracted with ether, which is then stripped off leaving solid product.

121 g (1 mol) of 1-azabicyclo[3,3,0]octa-2,4-diene-6-one is added in small increments to a solution of 3 equivalents of sodium bis[2-methoxyethoxy]-aluminum hydride, $[NaAlH_2(OCH_2CH_2OCH_3)_2]$, (Vitride$^R$) dissolved in THF. The reaction is allowed to proceed overnight at room temperature (about 20° C.) with stirring, after which the reaction mixture is heated to 50° C. and maintained at this temperature for 1 hr on an oil bath. The reaction mixture is then cooled to room temperature and toluene added to dissolve any solids in the mixture.

Only enough water to decompose the hydride is then added, and the organic layer is decanted from the aluminum sludge. The organic layer is washed with a saturated NaCl solution, then passed through a mass of solid sodium sulfate crystals. The organic solvent is then stripped to leave a dry solid which is sublimed to purify it. The yield is about 67% of theoretical.

An elemental analysis by nuclear magnetic resonance (nmr) spectroscopy confirmed the structure of the product to be 1-azabicyclo[3,3,0]octa-2,4-diene which is represented by the following structure:

(XXV)

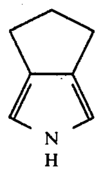

1-azabicyclo[3,3,0]octa-2,4-diene-6-one

EXAMPLE 2

Preparation of a polypyrrole ("PP") linked through N-adjacent C atoms, the PP having the structure:

(XXVI)

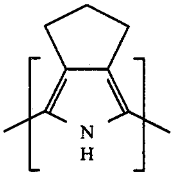

poly[1-azabicyclo[3,3,0]octa-2,4-diene-6-one

In a glass reaction vessel is placed a solution containing 700 ml of propylene carbonate, 23.4 g of tetrabutylammonium hydrogen sulfate and 35.2 g of 1-azabicyclo[3,3,0]octa-2,4-diene. Two palladium electrodes each having a surface area of about 75 $cm^2$ were placed in the solution about 2 cm apart. A total current flow of 38 amp. min. was passed through the solution. A black solid is deposited on the anode. After about 4 hr, the anode is removed by impinging a jet of MeCN on the electrode surface, and the electrode is rinsed thoroughly with MeCN. A black powdery deposit is thus removed from the electrode and the powder is then allowed to soak in 50 ml MeCN for about 16 hours. The MeCN and solid are then filtered and dried in a vacuum oven at about 120° C. for 16 hr. The dry weight of solid is 2.5 g.

The solid is found to be compactable. A sample of the black solid is pressed into a thin disc using a plunger type mold in which the pressure exerted is from about 15,000 psi. Powder PP so obtained is compactable at pressures as low as 5000 psi and even longer except that at such lower pressures the disc obtained is so fragile that it is difficult to handle routinely. Pressure above about 15,000 psi does not appear to result in substantially higher density than about 1.4 g/cc as determined by flotation in a liquid of matched density. Other PPs of this invention have a density in the range from about 1.1 to about 1.5 g/cc. Electrical conductivity of a disc having a thickness in the range from about 0.03 to about 0.05 cm, using the van der Pauw technique (*Phillips Tech. Rev.* 20 320, 1958), was found to be 0.25 S/cm; and for wire which was formed by compacting the powder into a groove milled in chlorinated poly(vinyl chloride), the conductivity was 0.12 S/cm. This latter numerical result was derived from a standard four-point conductivity measurement.

Analysis of the black solid confirmed the structure to be that given hereinabove.

| Elemental analysis: | | | | |
|---|---|---|---|---|
| | $[(XXVI)]_1\ [HSO_4^-]_{0.25}\ [H_2O]_{0.35}\ [C_4H_6O_3]_{0.25}$ | | | |
| Calculated | C = 59.57 | H = 5.91 | N = 8.72 | S = 4.97 |
| Found | C = 59.54 | H = 5.75 | N = 8.67 | S = 4.97 |

The ratio of the aforespecified moieties associated with a single repeating unit (XXVI) of the polymer was derived by attributing the S in the elemental analysis to the $HSO_4^-$ion, and adjusting the remainder between the residue of propylene carbonate $[C_4H_6O_3]$ solvent which contains a little water, and the trace of water which is known to be associated with the polymer in a somewhat similar manner as in a hydrate.

The polymers having the structure (XXVI) are particularly useful for conductivity control in solid-state micro circuits.

When the polymer is held in methylene chloride for an extended period of time it is found to be very slightly soluble, as judged from the discoloration of the liquid. This discolored solution is used to make an estimate of the molecular weight of the polymer, and as one skilled in the art will recognize, such an estimate is only very appropriate.

I claim:

1. A substituted pyrrole having the structure

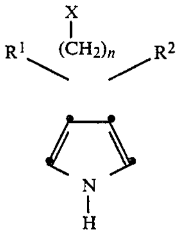

wherein, n is an integer chosen from 3 to 4, so that at least one C atom carrying the substituent in the polymethylene ring is not adjacent to the 3- and 4- C atoms on the pyrrole ring;

$R^1$ and $R^2$, if present, are independently selected from phenyl, hydroxyphenyl, cycloalkyl having from 4 to 7 carbon atoms, lower alkyl, alkoxy and hydroxyalkyl each having from 1 to about 6 carbon atoms, and each substituent may be on the same C atom, or different C atoms, and both $R^1$ and $R^2$ cannot be on C atoms adjacent to the 3- and 4- C atoms of the pyrrole ring; and, X, if present, is selected from the group consisting of

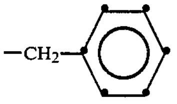

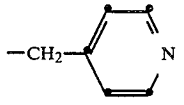

$=CH(C_{n'}H_{2n'+1})$

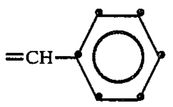

-continued

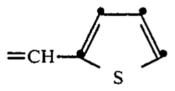

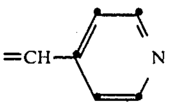

and fluorenylidene; n' is 2 to 4.

2. A substituted pyrrole having a structure selected from:

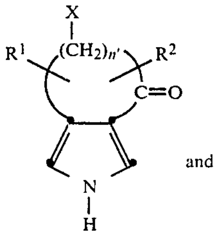

and

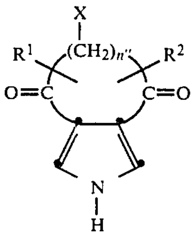

wherein, n' is an integer chosen from 2 and 3, n'' is an integer chosen from 2 and 3, so that at least one C atom carrying the substituent in the polymethylene ring cannot be adjacent to the 3- and 4- C atoms on the pyrrole ring;

$R^1$ and $R^2$, if present, are independently selected from phenyl, hydroxyphenyl, cycloalkyl having from 4 to 7 carbon atoms, lower alkyl, alkoxy and hydroxyalkyl each having from 1 to about 6 carbon atoms, and each substituent may be on the same C atom, or different C atoms, and both $R^1$ and $R^2$ cannot be on C atoms adjacent to the 3- and 4- C atoms of the pyrrole ring; and,

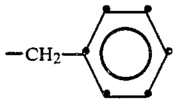

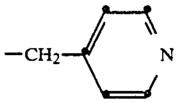

$=CH-(C_nH_{2n+1})$

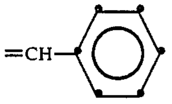

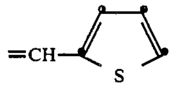

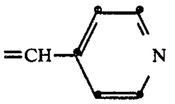

and fluorenylidene.

3. The substituted pyrroles of claim 2, including:

1-azabicyclo[3,3,0]octa-2,4-diene-6-one;

1-azabicyclo[3,4,0]nona-2,4-diene-6,9-dione;

7-phenyl-1-azabicyclo[3,3,0]octa-2,4-diene-6-one;

7-methoxy-8-methyl-1-azabicyclo[3,3,0]octa-2,4-diene-6-one;

7-dimethyl-1-azabicyclo[3,3,0]octa-2,4-diene-6-one;

7-benzyl-8-methyl-1-azabicyclo[3,3,0]octa-2,4-diene-6-one;

7-methyl-8-benzyl-1-azabicyclo[3,4,0]nona-2,4-diene-6,9-dione;

7-(4-pyridylmethyl)-1-azabicyclo[3,3,0]octa-2,4-diene-6-one;

bis[7,8-benzylidene]-1-azabicyclo[3,4,0]nona-2,4-diene-6,9-dione;

7-propylidene-1-azabicyclo[3,3,0]octa-2,4-diene-6-one;

7-(2,4,7-trinitro-9-fluorenylidene)-1-azabicyclo[3,3,0]octa-2,4-diene-6-one; and, 7-(2-thiophenomethylene)-1-azabicyclo[3,3,0]octa-2,4-diene-6-one.

* * * * *

UNITED STATES PATENT AND TRADEMARK OFFICE
CERTIFICATE OF CORRECTION

PATENT NO. : 4,602,090

DATED : July 22, 1986

INVENTOR(S) : Lee Traynor

It is certified that error appears in the above-identified patent and that said Letters Patent is hereby corrected as shown below:

Column 15, Claim 1, lines 30 to 40, the chemical structure should appear as shown below.

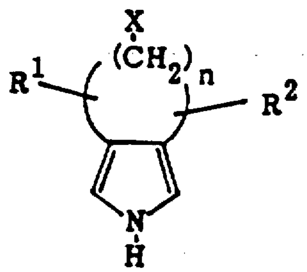

Signed and Sealed this

Eleventh Day of November, 1986

*Attest:*

DONALD J. QUIGG

*Attesting Officer* *Commissioner of Patents and Trademarks*